United States Patent [19]

Hanson

[11] Patent Number: 5,178,632
[45] Date of Patent: Jan. 12, 1993

[54] BI-LEAFLET HEART VALVE PROSTHESIS

[76] Inventor: Richard D. Hanson, 205 E. Woodley, Northfield, Minn. 55057

[21] Appl. No.: 895,844

[22] Filed: Jun. 9, 1992

[51] Int. Cl.⁵ ............................................... A61F 2/24
[52] U.S. Cl. ..................... 623/2; 137/512.1; 137/527
[58] Field of Search .................. 623/2; 137/512.1, 527

[56] References Cited

U.S. PATENT DOCUMENTS

| | | | |
|---|---|---|---|
| 4,178,639 | 12/1979 | Bokros | 623/2 |
| 4,276,658 | 7/1981 | Hanson et al. | 623/2 |
| 4,373,216 | 2/1983 | Klawitter | 623/2 |
| 4,451,937 | 6/1984 | Klawitter | 623/2 |
| 4,605,408 | 8/1986 | Carpentier | 623/2 |
| 4,822,353 | 4/1989 | Bokros | 623/2 |
| 4,892,540 | 1/1990 | Vallana | 623/2 |
| 5,061,278 | 10/1991 | Bicer | 623/2 |
| 5,080,669 | 1/1992 | Tascon et al. | 623/2 |

FOREIGN PATENT DOCUMENTS 0050971  5/1982  European Pat. Off. ............... 623/2

*Primary Examiner*—Ronald Frinks
*Attorney, Agent, or Firm*—Clayton R. Johnson

[57] ABSTRACT

The heart valve prosthesis has a generally annular base that has an annular body and diametrically opposite chordal segments having generally parallel flat surfaces. Each chordal segment has a pair of spherical recesses opening through the flat surface, the spherical recesses having ears of a pair of leaflets pivotally extending therein for movement between valve open and closed positions. For improving blood flow characteristics, each chordal segment has an upstream conical surface that is tapered generally radially inwardly in a downstream direction and a downstream conical surface that is tapered generally radially inwardly in an upstream direction. The conical surfaces intersect the flat surfaces. The leaflets have adjacent generally flat edges and arcuately curved edges that have parts remote from the leaflet pivot axes abuttable against the generally constant diameter wall portions of the annular body for limiting movement of the leaflets in a closing direction and stop members on the chordal segments to limit the movement of the leaflets in an opening direction.

14 Claims, 4 Drawing Sheets

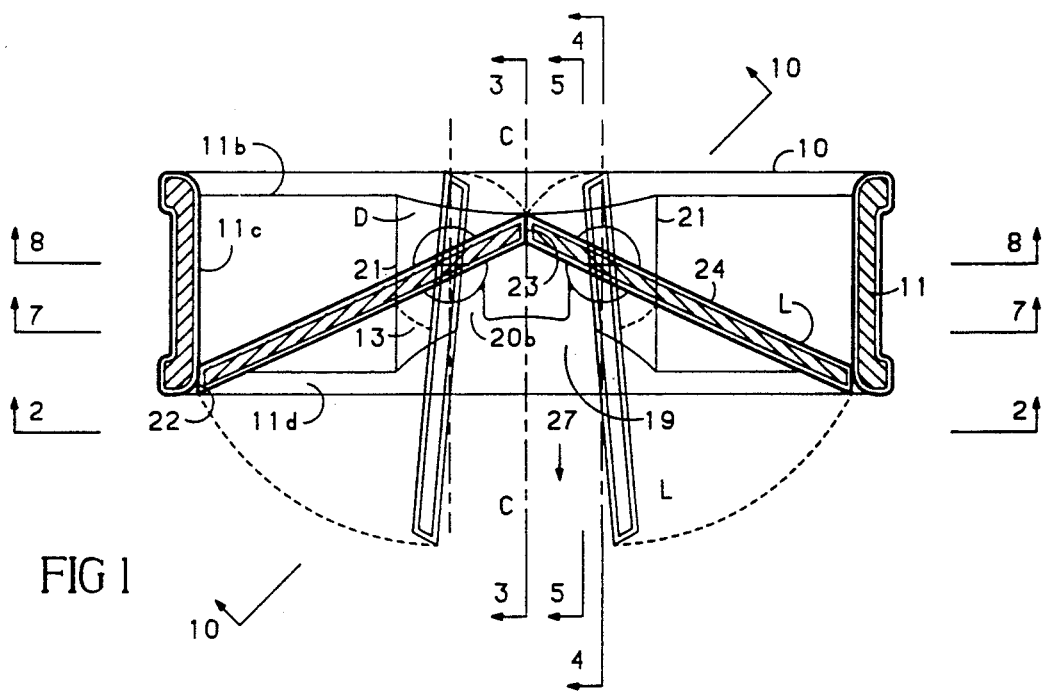
FIG 1
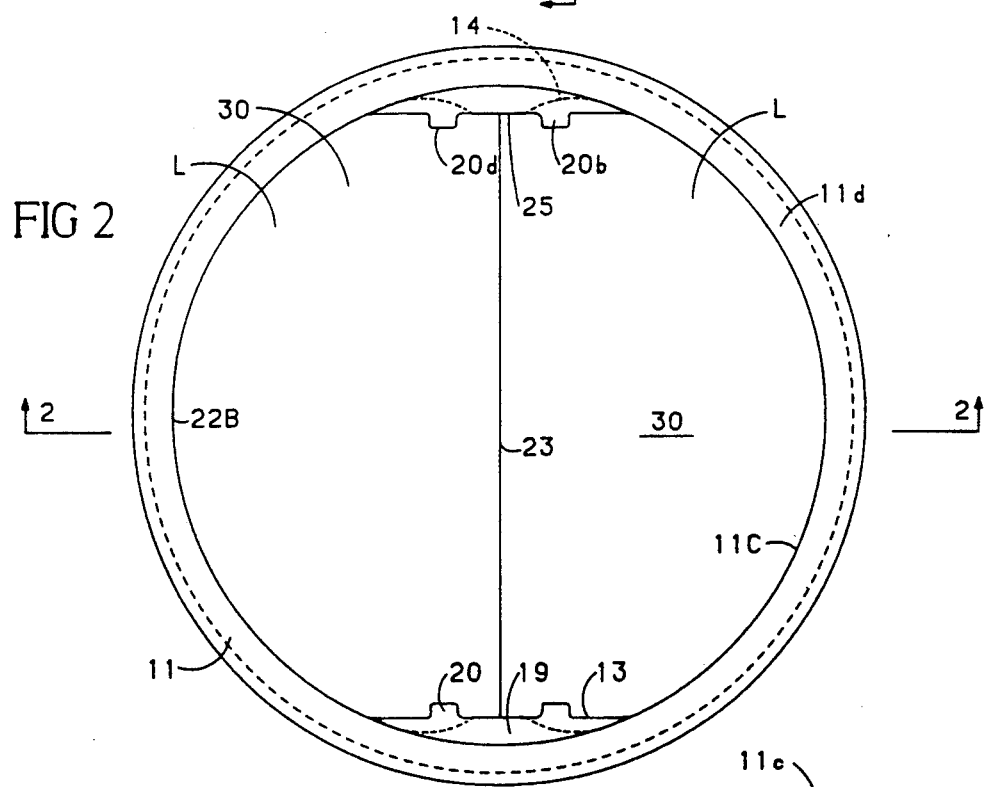
FIG 2
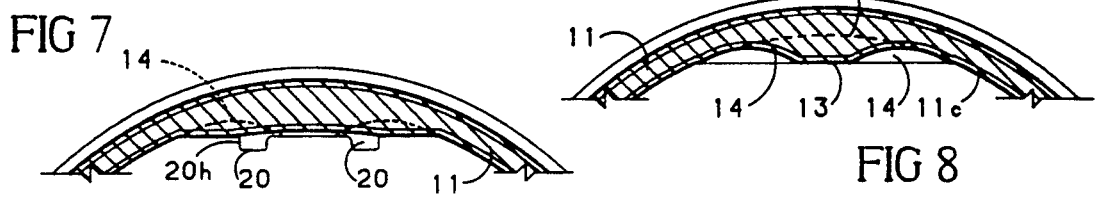
FIG 7
FIG 8

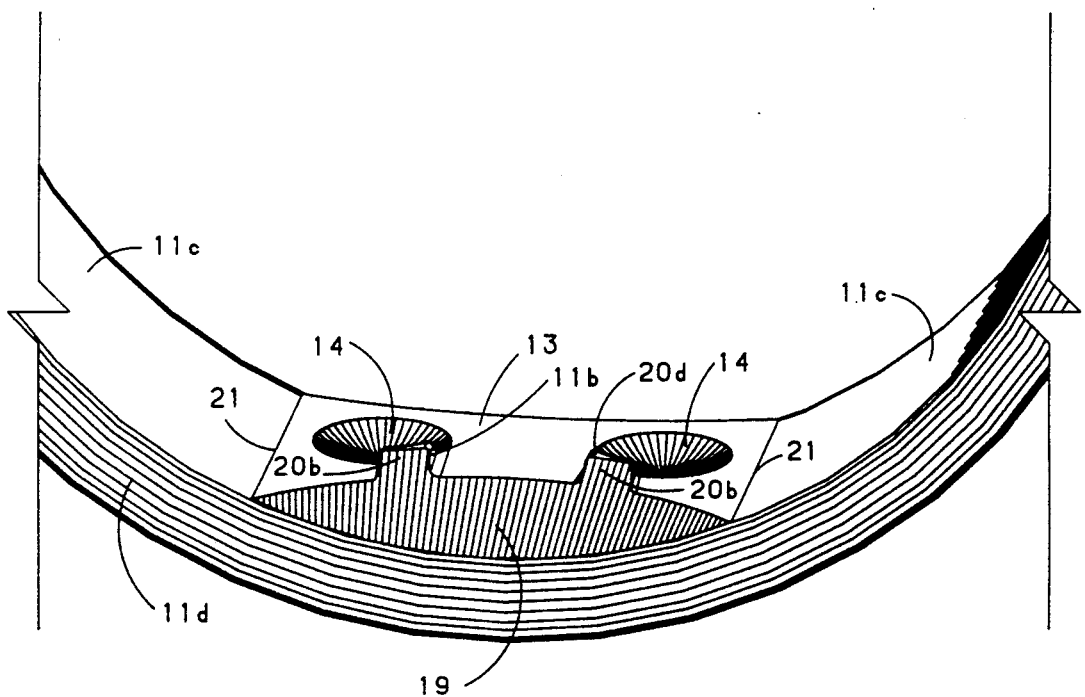
FIG II

BI-LEAFLET HEART VALVE PROSTHESIS

BACKGROUND OF THE INVENTION

A heart valve prosthesis with a pair of pivotally mounted leaflets for replacing defective natural heart valves.

Heart valve replacements have been known to extend human life by providing improved blood circulation. Many different types of artificial heart valves have been made, for example a ball in a cage, the flat single disc, the conical disc, the flat bi-leaflet, the curved bi-leaflet, and the tissue valve.

In U.S. Pat. No. 4,178,639 to Bokros, diametrically opposite supports extend upwardly of an annular base and have spherically recessed portions for receiving the leaflet pivot ears. The surfaces for stopping the leaflets in the open position are located above the base, as are the leaflet pivot ears. The base has a circular edge for acting as a stop when the leaflets move toward their valve closed position.

U.S. Pat. No. 5,061,278 to Bicer discloses an annular base having axially intermediate bores extending radially therethrough for mounting bearing inserts. Each valve member has opposite axle members pivotally extending into opposite bearing inserts, the valve members in their closed position being curved in the direction of extension of one valve member from the other. This can result in eddies and turbulence in blood flow. Further, the structure for pivotally mounting the leaflets provides grooves around the pivot where thrombic tissue can form.

U.S. Pat. No. 4,451,937 to Klawitter discloses an annular base having diametrically opposite chordal segments that appear to have parallel flat surfaces with arcuate depressions formed therein to have generally rectangular ears of the flat leaflets extended thereinto. Peg-like protrusions that extend into the blood passage arcuately intermediate the chordal segments to limit movement of the leaflets to their closed position would act to obstruct blood flow.

Each of the known prior art artificial heart valves displays certain deficiencies that are peculiar to their own design. In order to minimize or overcome various deficiencies of prior art heart valves, this invention has been made.

SUMMARY OF THE INVENTION

The heart valve prosthesis has an annular base having an annular body portion and diametrically opposite chordal segments joined to the annular body portion. The chordal segments have transversely adjacent recesses for pivotally receiving the ear portions of the leaflets therein, the recesses being axially intermediate the annular inlet and outlet edges of the tubular portion. The segments have generally parallel flat surfaces, other than for the recesses and the radially inwardly extending stop members that are joined thereto, and conically tapered surfaces that extend axially from the flat surfaces to the axially adjacent annular inlet and outlet edges of the annular body. The stop members limit the pivotal movement of the leaflets in an opening direction while the arcuate edge portions of the leaflets in abutting against the tubular portion in part limit the pivotal movement in a closing direction. Also the adjacent linear edges of the leaflets in abutting act in limiting the pivotal movement of the leaflets in a closing direction.

One of the objects of this invention is to provide new and novel heart valve prosthesis for minimizing the number of blood flow obstructions and surfaces on which material could collect during blood flow. Another object of this invention is to provide in heart valve prosthesis, new and novel mounting of leaflets to minimize opening and closing response time together with minimizing obstruction and modification of the flow of blood. An additional object of this invention is to provide new and novel heart valve prosthesis of a geometric construction to facilitate manufacturing, including machining, to reduce the cost of production.

BRIEF DESCRIPTION OF THE DRAWINGS

FIG. 1 is an axial cross sectional view of the heart valve prosthesis of this invention that is generally taken along the line and in the direction of the arrows 2—2 of FIG. 1, said view showing the leaflets in their closed position in solid lines and their fully open position in dotted lines;

FIG. 2 is a downstream view of the heart valve prosthesis that is generally taken along the line and in the direction of the arrows 2—2 of FIG. 1;

FIG. 7 is a fragmentary transverse cross sectional view of one of the chordal segments that is generally taken along the line and in the direction of the arrows 7—7 of FIG. 1;

FIG. 8 is a fragmentary transverse cross sectional view of one of the chordal segments that is generally taken along the line and in the direction of the arrows 8—8 of FIG. 1;

FIG. 11 is a fragmentary perspective view of the heart valve prosthesis.

Figure 3:
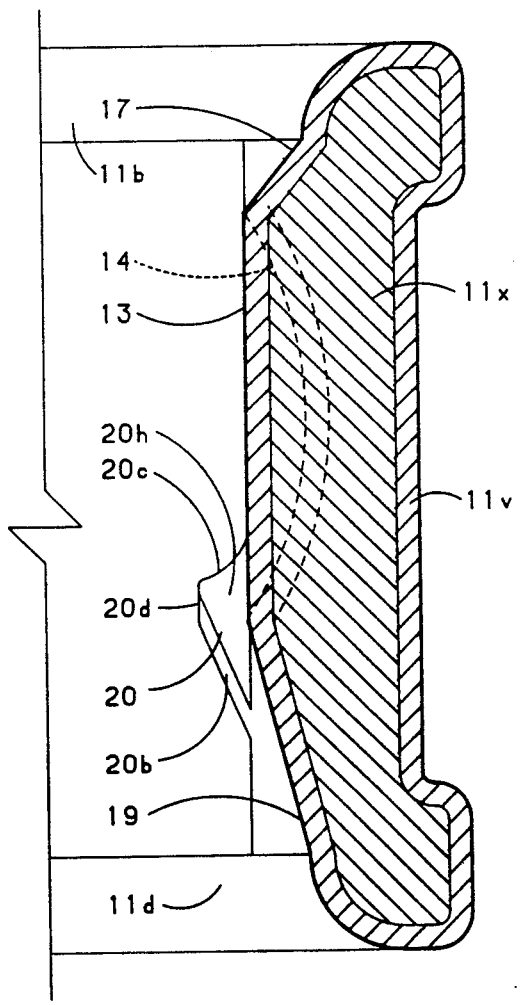
FIG. 3 is an enlarged axial cross sectional view that is generally taken along the line and in the direction of the arrows 3—3 of FIG. 1.
Figure 5:
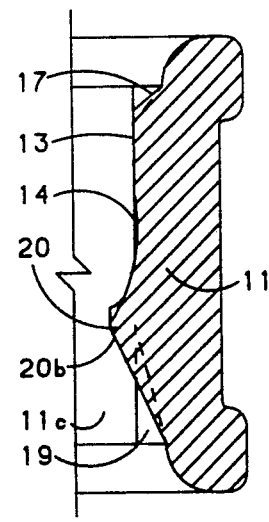
FIG. 5 is an axial cross sectional view that is generally taken along the line and in the direction of the arrows 5—5 of FIG. 1.

Referring in particular to FIGS. 1-3, the heart valve prosthesis includes an annular (ring) base, generally designated 10, having an annular body 11 with diametrically opposite chordal segments D integrally joined thereto define a blood passage therethrough. The annular body has annular upstream and downstream, rounded annular edge portions 11b and 11d respectively and substantially constant diameter inner peripheral wall portions (circular cylindrical wall portion) 11c extending axially between edge portions 11b, 11d and arcuately between the chordal segments D. The edge portion 11b has a generally planar annular part that is most axially remote from edge portion 11d and generally parallel to the planar annular part of edge 11d that is axially most remote from edge portion 11b, these parts being in planes that are substantially parallel to one another and perpendicular to the central axis c—c of the annular body.

There are provided two chordal segments D that are diametrically opposite one another, the chordal segments having adjacent surfaces 13 that are flat. Each flat surface 13 intersects the annular body cylindrical surface 11c along parallel axial lines 21 that are parallel to the central axis c—c. The diametric spacing of the flat surfaces 13 is significantly less than the diameter of the inner peripheral surface portions 11c. Each segment has a pair of transversely spaced spherical recessed portions 14 that open toward one another through the segment flat surface, are axially intermediate edges 11b, 11d nd are more closely adjacent to surface 11b than surface 11d. The recessed portions pivotally mount the spherical ear portion 15 of the respective one of the pair of valve member leaflets for pivotal movement between a valve open position and a valve closed position.

Each chordal segment has an upstream conical surface portion 17 that intersects with the body edge portion 11b and is tapered to extend generally radially inwardly toward the central axis c—c of the annular body in a downstream direction (arrow 27). Similarly each chordal segment has a downstream conical surface portion 19 that intersects with the body edge portion 11d and is tapered in an upstream direction to extend generally radially inwardly toward the central axis c—c of the annular body. Desirably each conical surface portion is generated about a cone axis that lies in a plane containing the central axis and bisecting the chordal segments. Further, desirably each conical surface portion intersects the respective flat surface portion, other than for the interruption by the stop members 20, along an arcuately curved line that at least substantially arcuately extends from one line 21 to the adjacent line 21. The maximum axial dimension of surface 19 is substantially greater than the corresponding dimension of the surface 17. Advantageously each conical surface is generated about a cone central axis that is parallel to the annular body central axis. Also, advantageously the upstream conical surface may be tapered to extend radially outwardly and toward the upstream annular edge portion at an angle of about 60 degrees, and the upstream conical surface may be tapered to extend radially inwardly and toward the upstream annular edge portion at an angle of about 15 degrees.

Figure 6:
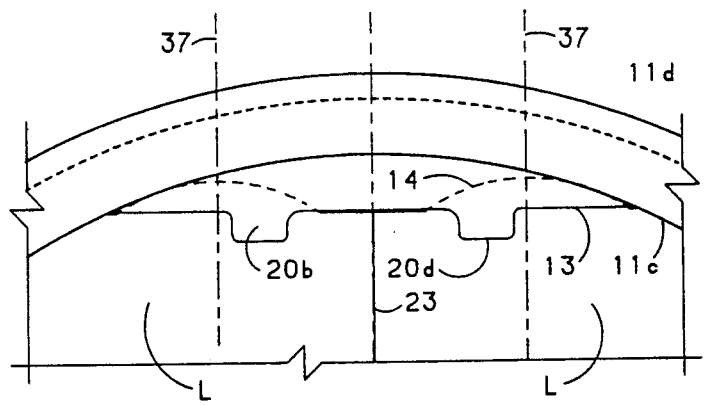
FIG. 6 is a fragmentary enlarged downstream view of the heart valve prosthesis base to more clearly show one of the chordal segments and the stop members joined thereto.
Figure 4:
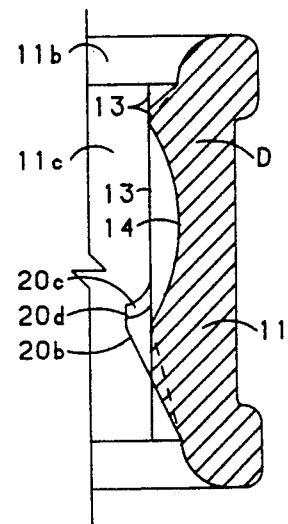
FIG. 4 is an axial cross sectional view that is generally taken along the line and in the direction of the arrows 4—4 of FIG. 1.

Each chordal segment has a pair of transversely spaced stop members 20 that are axially more closely adjacent to the downstream edge portion 11d than to the upstream edge portion 11b and at their maximum transverse spacing are more closely adjacent to one another than the corresponding spacing of the pivot axes of the leaflets; and extend radially more closely adjacent to the diametric opposite chordal segment flat surface than the segment to which it is joined to. The stop members have radially inner, axially extending surfaces 20b that are conically tapered to form an axial continuation of the respective conical surface 19 (see FIG. 4). Further the stop members have spherical surface portions 20c that form a continuation of the surface defining the recesses and transversely arcuately curved surface portions 20d. The surfaces 20d are more closely adjacent to the central axis c—c than the respective segment flat surface and any other part of the respective stop member. The remote axial surfaces 20h of the stop members that are bound by the surfaces 13, 20b, 20c 20d form stop surfaces that are abutted against by the leaflets to limit the movement of the leaflets to their fully open position as shown in dotted lines in FIG. 1.

Figure 9:
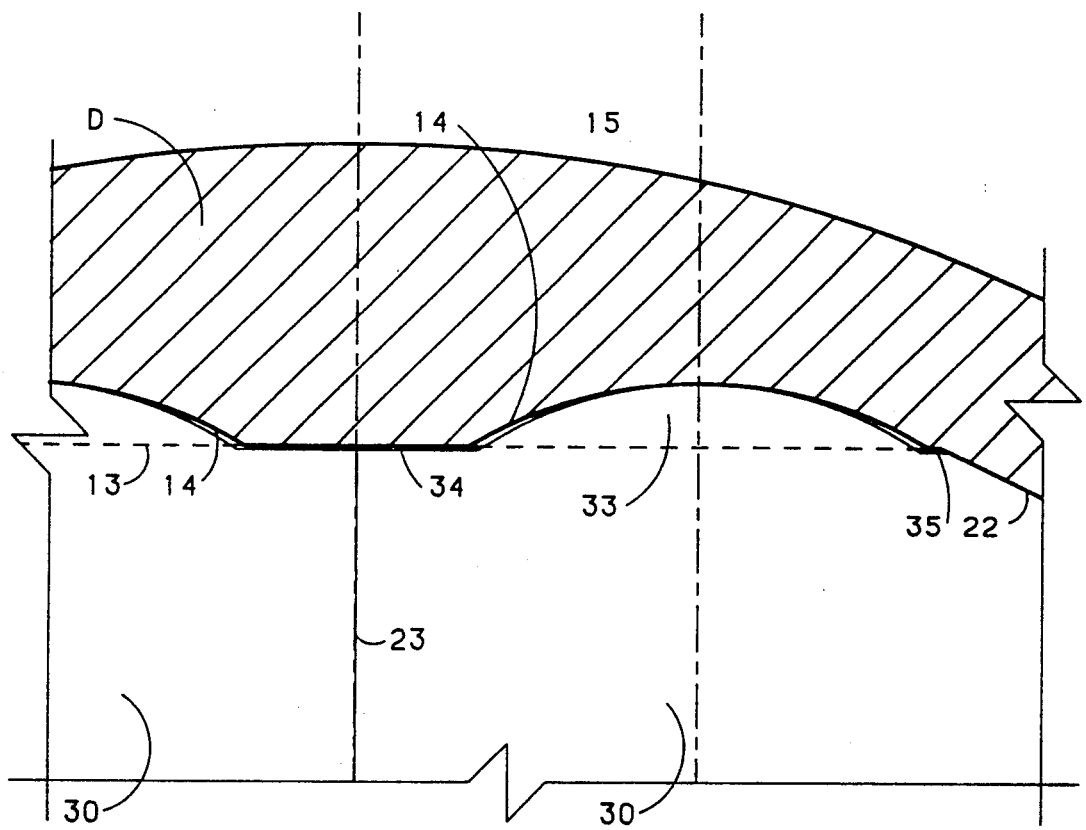
FIG. 9 is an enlarged fragmentary cross sectional view of a part of FIG. 8 showing the mounting of one of the leaflet ears and a portion of the other leaflet that is broken away.
Figure 10:
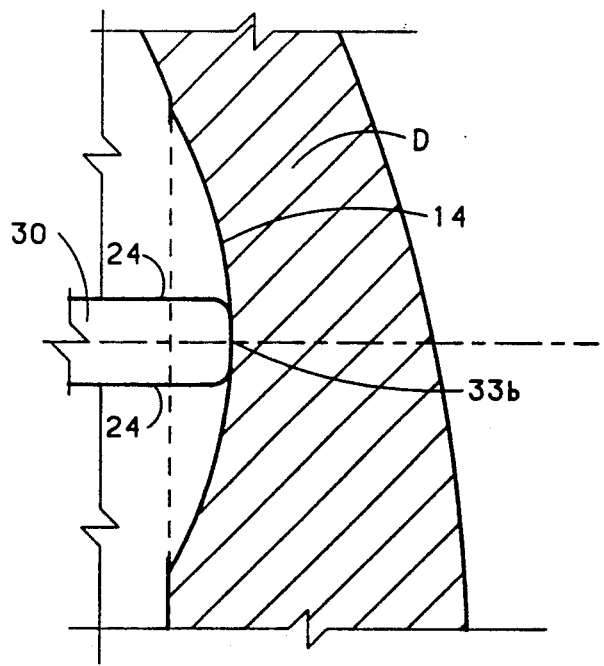
FIG. 10 is an enlarged fragmentary cross sectional view that is generally taken along the line and in the direction of the arrows 10—10 of FIG. 1.

The leaflets L have main bodies 30 that include adjacent elongated planar edges 23 that abut against one another in the valve closed position and extend at an angle to the upstream planar (flat) surfaces 24 of the respective leaflet. Further, each leaflet main body has a generally cylindrical, peripheral edge 22 arcuately extending from closely adjacent to one flat surface 13 to the other flat surface, and a flat planar edge 35 extending from the adjacent terminal end of edge 22 to the adjacent ear portions 33 and planar edge portions 34 extending between edge portion 23 and the ears 33 which are joined to the main body to extend away therefrom in the direction of the extension of the edges 23. Edges 34, 35 extend perpendicular to the respective edge 23, parallel to the surfaces 13 and closely adjacent to the respective chordal segment. Edges 22, other than for an arcuate part 22b remote from the edges 23, are arcuately curved to form a close fit with the axial wall 11c to permit the leaflets pivoting to their closed positions while the remote part 22b is arcuately curved to abut against the wall 11c axially adjacent to the edge 11d and arcuately intermediate the chordal segments to limit the closing movement of the leaflets to the position shown in FIG. 1. The peripheral edges 33b of the ears are spherically curved as may be seen from FIGS. 9 and 10. That is, in planes parallel to the leaflet surfaces 24 that extend between edges 22, 23, the peripheral edges of the ears are circularly curved. Similarly in planes that are perpendicular to the planes referred to in the preceding sentence and parallel to the leaflet pivot axes 37, the peripheral edges of the ears are circularly curved; and thus the ear edges are spherically curved. The leaflets may be installed by deforming the base, moving the leaflets to have the ears adjacent to the spherical recesses and allowing the base to resume its original shape.

As an example of the invention, advantageously the leaflets extend downwardly at an angle to the horizontal of about 20-30 degrees in their closed position and preferably about 25 degrees. The leaflets in pivoting between their open and closed positions, preferably pivot through an angle of about 60 degrees. Advantageously when the leaflets are in their fully open position they converge toward one another in an upstream direction with each leaflet extending toward the other at an included angle of about 5 degrees relative to the horizontal.

With the annular base having axially opposite, generally planar edges, there is no protrusion extending upwardly into the atrium to cause obstruction or modification of blood flow through the base. The base has a central flow passage that provides for uniform blood movement. The pivot areas are blood washed clean due to the manner of pivotally mounting the leaflets and the leaflet movement as well as the blood flow. The upstream and downstream conical surfaces of the chordal segments improve blood flow and surface washing while decreasing turbulence.

The provision of the partial spherical shaped edges on the ears of the leaflets pivotally bearing against the spherical shaped recesses provides for wear distribution and thereby long life. Since the angle of pivotal movement of the leaflets is limited by abutting against the downstream end portion of the base arcuately intermediate their pivots and alternately by the stop members that are located downstream of the pivot axes, the response time for the movement of the leaflets to their closed position is held to a minimum.

The heart valve may be made from a variety of acceptable materials, for example titanium. As another example the base may have a core 11x made of, for example graphite, and a pyrolytic carbon coating 11v that covers the entire core (see FIG. 3). The leaflets may be similarly coated. The coating has been shown only in FIG. 3, however, it is to be understood that if coated, the cross sectional showing of parts of the heart valve prosthesis would have a core and a coating. Alternately the base may be made of metal without a coated core and the leaflets of a pyrolytic material.

As an example the minimum axial dimension between the upstream and downstream conical surfaces may be about half of the maximum axial dimension of the base and the maximum radial dimension of a chordal segment may be about the same as the minimum wall thickness of the annular body and greater maximum corresponding dimension of each stop member.

What is claimed is:

1. A heart valve prosthesis, comprising a base having an annular body that has a central axis, an upstream annular edge portion and a downstream annular edge portion, and diametrically opposite chordal segments integrally joined to the annular body that have generally flat surfaces that are parallel to one another and the central axis, the flat surfaces being axially intermediate the body edge portions, each chordal segment having an upstream conical surface part that intersects the upstream edge portion and is tapered toward the other chordal segment in a direction axially toward the downstream annular edge portion to intersect the flat surface and a downstream conical surface part to intersect the downstream edge portion and the flat surface, first and second leaflets mounted for movement between valve open and closed positions, the leaflets and the chordal segments having cooperating means for mounting the leaflets for pivotal movement about parallel axes between the leaflet positions, and stop means on the chordal segments for limiting the pivotal movement of the leaflets from their closed position to their open position.

2. The heart valve prosthesis of claim 1 further characterized in that each body edge portion has a terminal edge part that is annular and substantially parallel to the other.

3. The heart valve prosthesis of claim 1 further characterized in that the leaflets have adjacent, generally parallel edges and that the cooperating means comprises oppositely extending pair of leaflet ears and a pair of chordal segmental recesses for each chordal segment and opening though the respective chordal segment flat surface.

4. The heart valve prosthesis of claim 1 further characterized in that the annular body has substantially constant diameter inner peripheral wall portions extending arcuately between the chordal segments and that each flat surface intersects the inner peripheral wall portions along transversely spaced axial lines.

5. The heart valve prosthesis of claim 4 further characterized in that the upstream conical surface part intersects the flat surface along an arcuately curved line that extends transversely from one of the axial lines to the other for the same segment.

6. The heart valve prosthesis of claim 4 further characterized in that the stop means comprises a stop member on each chordal segment, the stop member of each chordal segment having a conical surface portion that forms a smooth continuation of the respective downstream conical surface part and that each body edge portion has a terminal edge part that is annular and substantially parallel to the other.

7. The heart valve prosthesis of claim 1 further characterized in that each body edge portion has a terminal edge part that is annular and substantially parallel to the other, that the leaflets have adjacent, generally parallel edges and that the cooperating means comprises oppositely extending pair of leaflet ears and a pair of chordal segmental recesses axially intermediate the body edge portions for each chordal segment and opening to the respective chordal segment flat surface.

8. The heart valve prosthesis of claim 7 further characterized in that the ears of each leaflet have a pivot axis that is substantially more closely adjacent to the upstream edge portion than the downstream edge portion.

9. A heart valve prosthesis, comprising a base having an annular body that has a central axis, an upstream annular edge portion and a downstream annular edge portion, each body edge portion having a terminal edge part that is annular and substantially parallel to the other body edge portion, and diametrically opposite chordal segments integrally joined to the annular body, each chordal segment having a generally flat surface portion that is parallel to the other and the central axis, the flat surfaces being axially intermediate the body edge portions annular parts, first and second leaflets mounted for movement between valve open and closed positions, the leaflets and the chordal segments having cooperating means for mounting the leaflets for pivotal movement about parallel pivot axes between the leaflet positions, the cooperating means including transversely spaced chordal segment spherical recessed portions axially between the upstream and downstream annular edge portions and leaflet ears extending into the adjacent recess portions, the ears having edges that are spherically curved for forming a close pivotal fit with the adjacent recessed portion, and stop means on the chordal segments for limiting the pivotal movement of the leaflets from their closed position to their open position, the stop means being located axially intermediate the downstream annular edge portion and the leaflets when the leaflets are in their closed position, the base being of a substantially constant inner diameter circumferentially between the chordal segments and axially between the upstream and downstream edge portions.

10. The heart valve prosthesis of claim 9 further characterized in that the ears and recesses provide leaflet pivot axes that are transversely spaced, parallel to one another and to the terminal edge parts, and axially more closely adjacent to the upstream annular edge portion, that each leaflet has a main body extending between the leaflet ears and has adjacent flat edges, each leaflet main body having an arcuate peripheral edge portion that has an arcuate part arcuately intermediate the ears for abutting against the constant diameter portion arcuately intermediate the chordal segment and axially intermediate the pivot axes and the downstream annular edge portion to limit the movement of the leaflet from its open position to its closed position, the leaflets in their closed position being inclined toward the downstream edge portion in a direction toward the leaflet peripheral edge portion part.

11. The heart valve prosthesis of claim 10 further characterized in that each leaflet has opposite planar surfaces extending between the arcuate peripheral edge and flat edge, including the ear portion edges.

12. The heart valve prosthesis of claim 9 further characterized in that each chordal segment has an upstream conical surface portion that intersects the upstream edge portion and the flat surface and a downstream conical surface portion that intersects the downstream edge portion and the flat surface.

13. The heart valve prosthesis of claim 12 further characterized in that the stop means comprises a stop member for each leaflet that is joined to one of the chordal segments to extend radially inwardly of the respective chordal segment flat surface and has a radial inner surface that is conically tapered generally radially inwardly in a direction axially toward the downstream edge portion.

14. The heart valve prosthesis of claim 12 further characterized in that the upstream conical surface portion is tapered to extend radially outwardly and axially toward the upstream annular edge portion at an angle of about 60 degrees, and that the downstream conical surface is tapered to extend radially inwardly and axially toward the upstream annular edge portion at an angle of about 15 degrees.

* * * * *